United States Patent [19]
Pranitis, Jr. et al.

[11] Patent Number: 5,860,806
[45] Date of Patent: Jan. 19, 1999

[54] SINGLE DOSE DENTAL ADHESIVE DELIVERY SYSTEM AND METHOD AND ADHESIVE THEREFOR

[75] Inventors: Leo J. Pranitis, Jr., Corona; Daniel Ng, Wildomar, both of Calif.

[73] Assignee: The Kerr Corporation, Orange, Calif.

[21] Appl. No.: 758,383

[22] Filed: Nov. 29, 1996

[51] Int. Cl.$^6$ ................................................. A61G 17/02
[52] U.S. Cl. ............................ 433/80; 433/89; 206/63.5
[58] Field of Search ................................. 433/80, 89, 90; 206/63.5

[56] References Cited

U.S. PATENT DOCUMENTS

| | | | |
|---|---|---|---|
| 4,551,135 | 11/1985 | Gorman et al. | 433/90 |
| 4,973,248 | 11/1990 | Sigler | 433/90 |
| 5,131,845 | 7/1992 | Feldman et al. | 433/104 |
| 5,240,415 | 8/1993 | Haynie | 433/216 |
| 5,348,988 | 9/1994 | Suh et al. | 523/118 |
| 5,538,129 | 7/1996 | Chester et al. | 206/63.5 |

FOREIGN PATENT DOCUMENTS

| | | |
|---|---|---|
| 0688541 | 12/1995 | European Pat. Off. . |
| 9202654 | 4/1992 | Germany . |
| WO9603326 | 2/1996 | WIPO . |

OTHER PUBLICATIONS

Translation of German utility model No. DE 9202654.
CRA Newsletter, p. 2, May, 1996, "Clinical Characteristics Comparison".
Perma–Quick™ Bonding System product literature of Ultradent Products, Inc., 1995.
Clearfil® Liner Bond 2 product literature of Kurray Co., Ltd., Dec. 1995.
OptiBond™ product literature of Kerr Corportation, 1996.
PCT Search Report, Date of Mailing May 11, 1998.

*Primary Examiner*—John J. Wilson
*Attorney, Agent, or Firm*—Wood, Herron & Evans, L.L.P.

[57] ABSTRACT

A dental adhesive delivery system provides a single usage amount of dental adhesive in a non-resealable container for use in treating a single patient. The packaged amount of adhesive may include up to the amount required to treat all of the teeth needing treatment of not more than a single patient, for example in the range of approximately 0.05 to 1.0 ml. The packaged amount may include a dose only large enough for the treatment of a single tooth or for the application of a single restoration, for example, in an amount of about 0.1 ml. The adhesive is one that includes a volatile solvent or other liquid carrier, such as, for example, water or an organic liquid such as acetone or alcohol. In the preferred embodiment, an alcohol based adhesive is provided having a filler of approximately 25% by weight. The single use container is preferably formed of injected molded plastic and includes a reservoir section that contains the adhesive and a break off section that surrounds an opening that receives a snap fit cap. A plastic and foil pouch constitutes a secondary containment volume or vapor seal which limits the escape of evaporated organic carrier or solvent. The cap and break off section are discarded and the adhesive is removed with the tip of a wand for application to the teeth of a patient, whereupon the container, which is not resealable, is discarded.

33 Claims, 1 Drawing Sheet

SINGLE DOSE DENTAL ADHESIVE DELIVERY SYSTEM AND METHOD AND ADHESIVE THEREFOR

This invention relates to the delivery of dental adhesives to practitioner-users for the treatment of dental patients, and, more particularly, to the combinations of adhesive containers and dental adhesives and to adhesive packaging and delivery techniques for adhesives particularly useful for affixing dental restorations to teeth.

BACKGROUND OF THE INVENTION

The application of dental restorations to the teeth of patients requires the use of specially formulated dental adhesives that will be effective to form a bond with a surface of the patient's dental anatomy. The more effective of the adhesives currently having the most widespread use include resins that are applied to a tooth surface, for example, and then cured with ultraviolet or visible light. With certain formulations of such light cure adhesives, a small amount of such light is sufficient to start an adhesive curing reaction that will propagate through the entire dose of adhesive. Other types of adhesives require larger exposures to such light for the cure of the entire body of the adhesive. Such adhesives are used for the bonding of more transparent or semi-transparent restorations, such as direct restorations, veneers and other thin, small or in situ formed composite restorations.

The more effective of the dental adhesives for the uses discussed above have been provided to dentists in multiple parts. The various parts of these multi-part adhesive systems take advantage of the different properties at different parts of the system at the different stages of their use. A first part of the system may include, for example a primer, which is painted onto an area of the tooth to which the restoration is to be attached. The primer dries the surface and penetrates to form a basis for an effective bond. A second part may include a filled or an unfilled resin that is applied over the first part to interact with it and form a bond. In some forms, the second part is itself supplied in two parts. In a superior form a subpart of the second part is a resin and the other subpart is a fill material in the form of minute glass beads. The fill, which is mixed to a content of about 48% of the mixture with the resin, contributes strength and shock absorbency to the bond. Multi-part adhesives of this type are available in an alcohol base and marketed under the trademarks Optibond and Optibond FL by Kerr Dental Materials Center of Orange, Calif.

The application of each part of the multi-part adhesive system by a dentist calls for the coating of a small area of a patient's tooth, for example, with a small quantity of each part of the adhesive system being applied. The coating with each adhesive part is followed by the placement of the restoration, which may be a restoration formed in a dental laboratory on a model of the patient's teeth that is transferred by the dentist onto the patient's dental anatomy or may be a restoration formed in situ by the dentist, usually from a composite material. The different parts of the multi-part adhesive systems are traditionally packaged in containers designed to hold a quantity of material sufficient for bonding multiple restorations and which can be resealed after each use. In a one part adhesive, a single container designed to hold a quantity of material sufficient for bonding multiple restorations in the treatment of multiple patients and which can be resealed after each use is used. To use such containers, the dentist or dental assistant is required to retrieve the containers for each part of the adhesive system from a storage area, open each container, dispense from each container into another container (typically a container which constitutes an open well) the required amount of the adhesive part being dispensed, reseal each container for each adhesive part and return the containers to the storage area.

If the adhesive system being used has multiple second parts, the different parts are generally dispensed into the same container well and mixed before application to the tooth. If the system is a one part adhesive, only one container must be opened.

After the adhesive parts have been applied to the tooth, the containers into which the adhesive parts were dispensed is generally disposed of.

The handling and use of multiple part adhesives is regarded by many dentists as inconvenient. With direct restorations particularly, the need to handle and mix separate parts of the adhesive is an inconvenience, in part because the composite material of which the restoration is formed also must be handled and mixed. While one part or premixed adhesives are available, such adhesives do not include fills or fluoride release and many are formulated with an acetone base. Acetone based adhesives tend to degrade after being opened as their solvent components tend to evaporate, altering the adhesive composition, and are regarded as less desirable by many dentists or patients.

One such acetone based adhesive is a one part adhesive comprised predominantly of an acetone solvent and a Penta-P adhesion promoter. The composition contains no fluoride release system or fillers. The adhesive is characterized by high shrinkage. Another one part adhesive that is available is comprised predominantly of an acetone solvent and a BPDM adhesion promoter. The adhesive also contains no fluoride release system or fillers. It provides only a medium bond strength and also is characterized by high shrinkage.

U.S. Pat. No. 5,348,988 discloses a dentin bonding system which utilizes unsaturated carboxy esters as bonding agents produced by the reaction of unsaturated alcohols with cyclic acid dianhydrides, with BPDM as part of the dentin bonding system. The system also comprises a dentin conditioner which is the reaction product of a cyclic acid anhydride with an ethylenically unsaturated alcohol, and a two-part dentin primer, the first part of which comprises the reaction product of an N-arylglycine with glycidyl methacrylate. The second part of the two-part dentin primer is selected from products such as BPDM. The patent also discloses the use of a solvent such as acetone. The composition is applied in solution to an area to which a bond is desired, and the bond is completed by use of a self-curing initiator or a light cure system. Other materials such as camphoquinone are disclosed as being useful. Premixed or one part adhesives that are water based are also available. The water based adhesives, while more stable than the acetone or alcohol based adhesives, require a predrying of the tooth area on which the adhesive is being applied, because moisture on the surface of the tooth can change the properties of the adhesive. Water based adhesives have also been found to be less strong.

The adhesives of the prior art that are discussed above possess a common problem of the evaporation of the product. This is particularly a problem with the one part organic solvent based adhesives, but is also true of water based and other solvent based adhesives. Such adhesives possess the desired composition upon the first opening of the bottle or container in which they are delivered, but before a substantial portion of the adhesive is used, evaporation of a portion of the solvent and other high volatility components occurs, leaving the balance of the adhesive with increased composition of the other components and increased viscosity. This change in concentrations adversely affects the application of the adhesive and the quality and resulting performance of the bond.

In addition, the use of bulk delivery systems for packaging one part adhesives has had several undesirable features. One such feature has been the multiple number of times that the container must be opened, handled and resealed. Each time the container is opened and handled, a potential exists for contaminating the entire contents of the container. For example, if the container is sealed with a cap which must be removed to dispense the adhesive, the cap may become contaminated if placed on a dental operatory tray or any other resting place while the contents of the container are being dispensed. When the cap is reset on the container to reseal it, the contents of the container may become contaminated. In addition, the dentist or dental assistant whose hands may have had contact with the mouth of a patient being treated may contaminate the cap while holding it or may contaminate the opening in the container through which the contents are dispensed.

Another undesirable feature of the bulk delivery system is that the dentist or dental assistant is required, each time the adhesive system is used, to accurately dispense the correct amount of adhesive from the container. If an insufficient amount is dispensed, the steps involved in dispensing the adhesive must be repeated. If an excessive amount of adhesive is dispensed, the excessive adhesive is wasted.

A further undesirable feature of the prior art systems is that they increase the opportunity for evaporation of portions of the adhesive. This can occur when the container holding the adhesive is unsealed. In the unsealed state, the adhesive is exposed to the atmosphere of the dental office. This can cause the portions of the adhesive to evaporate which will affect the performance of that portion of adhesive remaining in the container when it is later used. If the container remains unsealed for an extended period of time, an amount of the adhesive base sufficient to affect the performance of the adhesive may evaporate.

As a result of the above, there has been a demand for some time by dentists for adhesives that are more convenient, easier to use, and less susceptible to degradation prior to their use and for a delivery system that will preserve the purity of the adhesive, deliver a pre-measured amount of adhesive and reduce the likelihood of evaporation of the adhesive contents. Notwithstanding this demand, an effective combination of adhesive and container for delivery to the dentist has not been found. Accordingly, a need remains for an adhesive delivery system, particularly for use in applying dental restorations.

SUMMARY OF THE INVENTION

A primary objective of the present invention is to provide an improved method of delivering dental adhesive that overcomes problems of the prior art.

A further objective of the present invention is to provide a one part dental adhesive that is stable, effective and amenable to delivery by an improved method for application by a dentist.

It is a particular objective of the present invention to provide a combination of improved dental adhesive delivery system and improved dental adhesive particularly suitable for delivery thereby wherein the delivery system is particularly suitable for delivery of the improved adhesive.

According to the principles of the present invention, there is provided a single dose dental adhesive delivery system that is provided with a single dose one part dental adhesive and single dose adhesive container therefor that are useful for the bonding of dental restorations to the dental anatomy of patients, and for the application of direct dental restorations. The dose is that required for treatment of a single patient and may be only that for a single tooth or single restoration. The adhesive that is provided, particularly in the delivery system of the invention, is a one part dental adhesive provided in vapor sealed single dose packaging that maintains in a stable form an adhesive that is particularly suitable for single dose delivery.

According to the preferred embodiment of the invention, a two part container is preferably formed of injection molded plastic, one part of which an elongated body or container-like cup portion with a tubular bore therein having a single opening at one end and defining a cavity within that is large enough to contain a single dose of dental adhesive. The other part of the container is a closure or cap configured to plug the opening to seal the liquid adhesive into the cavity without leakage. A secondary or auxiliary seal is provided, either between or at the junction of the cap and the container portion or preferably by way a polyfoil pouch to contain the adhesive filled container. The lower end or tip of the cap portion of the container extends into the bore while occupying a portion of the volume of the bore to displace air therein, but leaves a sufficient volume to contain a measured single tooth dose of dental adhesive, for example in a preferred amount of about 0.1 milliliter, although a single patient dose having a volume of from about 0.05 ml to approximately 1 ml may be employed.

Further according to the preferred embodiment of the invention, the container is loaded with an adhesive that is formulated of an alcohol base and preferably also with a filler of between 20% and 30% by weight. Preferably, the adhesive for use with the delivery system, in accordance with the present invention, is a one part, one step, dental adhesive and is a visible light curable, methacrylate resin-based mixture of monomers capable of forming both chemical and mechanical adhesive bonds to both natural tooth structures and dental restorative materials. The adhesive composition includes a fast evaporating organic solvent or other liquid carrier component, preferably ethyl alcohol.

In its preferred form, each part of the container includes structure which, when the container is positioned with each of the parts in an opposite one of the dentist's hands, can be opened by a twisting action. The opening leaves the original interface between the cup and the cap in tack, but breaks the cup along a weak web adjacent an annular score line that encircles the cap near the top. The container is thus non-reusable. Twist grip structure is provided on each part in the form of fins or projections. The container includes a handle part that can be discarded along with the upper portion of the cup, leaving a body part of the cup that holds the cavity filled with the adhesive dose. The cavity is open at one end to allow for the removal of the adhesive. Preferably, a kit is provided that includes the container in combination with an elongated applicator having a sponge-like tip that can be dipped into the cavity, coated with adhesive, and then directed by the dentist upon the tooth or portion of the patient's dental anatomy to which the restoration is to be bonded. Adhesive is transferred from the applicator by swabbing the area with the tip of the applicator.

The delivery system of the invention provides for a single part dental adhesive, which, upon an opening of the container, is undegraded and of the intended composition at the time of the application of the dose. The one part adhesive that is provided is strong when applied and stable up to the point of use. The system frees the practitioner of the need to handle, mix or reseal the adhesive while performing the restorative treatment on the patient. The system retains the sterility of the adhesive until its use and reduces the likelihood of contamination of the supply prior to application of the adhesive to the patient.

These and other objectives and advantages of the present invention will be more readily apparent from the following detailed description of the of the preferred embodiments of the invention, in which:

DETAILED DESCRIPTION OF THE PREFERRED EMBODIMENT

Figure 1:
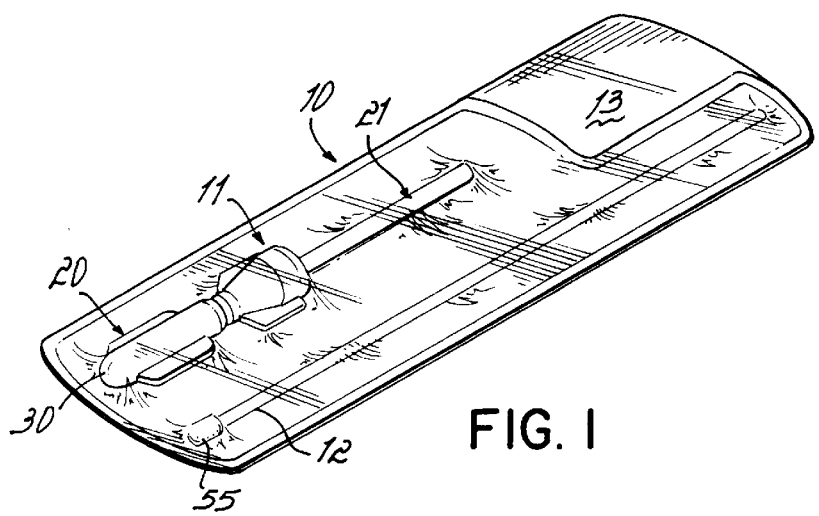
FIG. 1 is a perspective view of a preferred embodiment of a packaged single dose dental adhesive of the adhesive delivery system of the present invention.

FIG. 1 illustrates a single dose adhesive package 10 in accordance with the preferred embodiment of the dental adhesive delivery system of the present invention. The package 10 includes a filled single dose adhesive capsule 11 and an adhesive application wand 12 sealed in a plastic and foil pouch 13. The inclusion of the wand 12 in the package 10 is optional. The filled capsule 11 includes a single dose container 14 in which is contained a measured dose 15 of adhesive (FIG. 3), of approximately 0.1 milliliter in volume. The pouch 13 constitutes one preferred form of an auxiliary or secondary containment volume or vapor seal which limits the escape of evaporated organic carrier or solvent (e.g., alcohol) that might leak in vapor form from the container 14. The pouch 13 has a limited volume so that solvent vapor that escapes from the container 14 will reach an equilibrium in the gas within the pouch 13, prevent further loss of solvent from the adhesive 15 beyond an insignificant and acceptable amount. The pouch 13 is preferably a polyfoil material that may be formed of a thin layer of aluminum foil on each side of which is laminated a layer of plastic. Such a polyfoil that is in accordance with U.S. military specification MIL-B-131H Type 1 Class H is preferred. Alternatively, a film of completely plastic material with vapor barrier properties, which could be transparent, may be used, and this transparent type is illustrated in FIG. 1 for the convenience of illustrating the contents of the package 10. While other means of secondary or auxiliary seal can be employed, as discussed below, the use of such a pouch 13 fills the need for additional packaging to enclose the package 10 and to carry labeling and product information.

Figures 2, 3, 4, 5:
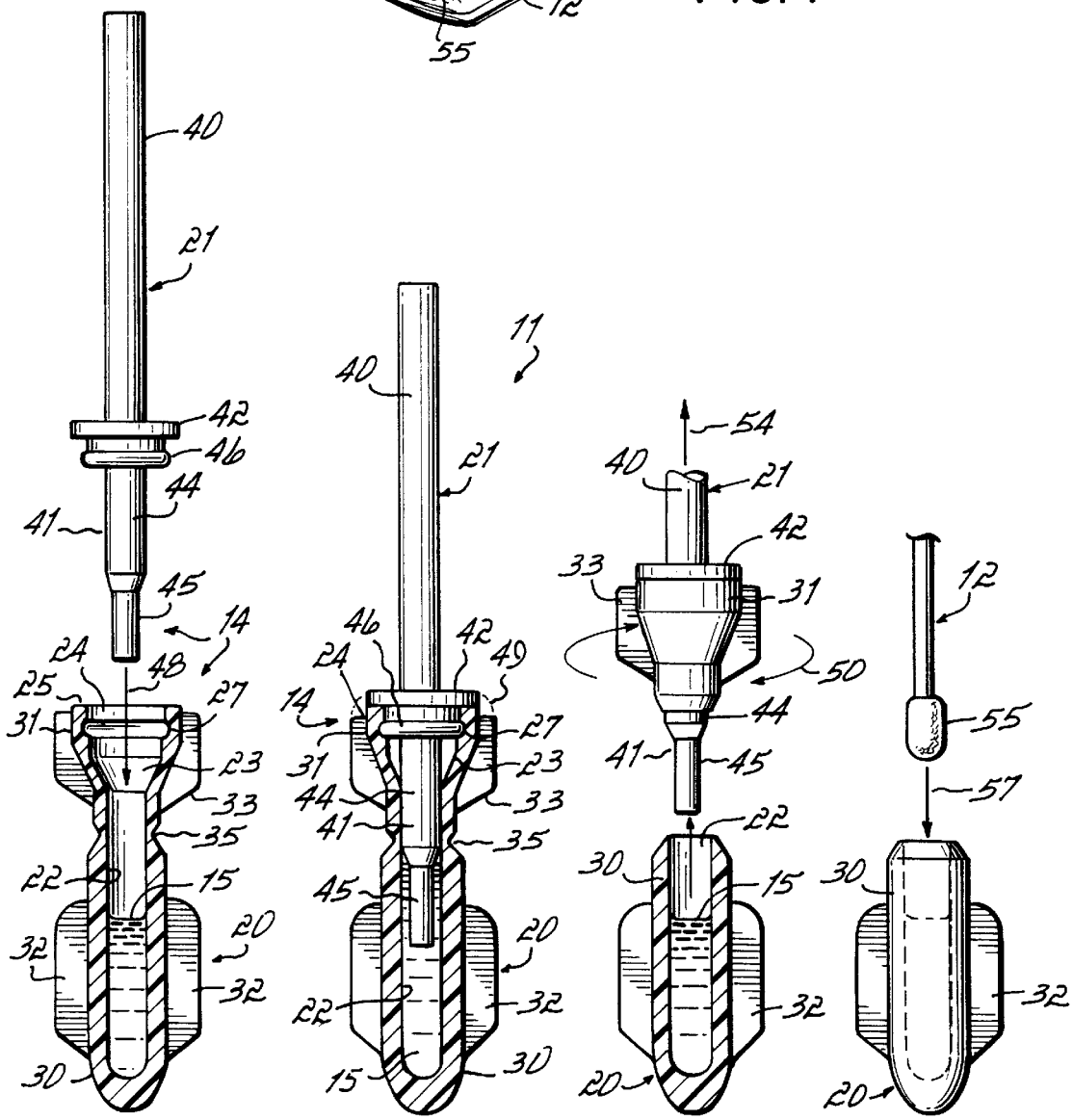
FIG. 2 is a side view, partially in cross-section, of an open one dose adhesive container of the delivery system of FIG. 1, as it appears at the time it is filled with adhesive.
FIG. 3 is a view, similar to FIG. 2, illustrating a filled and closed container of the delivery system of FIG. 1.
FIG. 4 is a view, similar to FIG. 2, illustrating the opening of the container of the delivery system of FIG. 1.
FIG. 5 is a side view of the reservoir portion of the container of FIG. 4 illustrating the open container with the adhesive ready for use.

The container 14 is illustrated in detail in FIG. 2. The preferred container 14 is described and illustrated in German Utility Model No. DE 9202654. The container 14 is formed of two molded thermoplastic parts, including an elongated cup 20 and a cap 21, both of a relatively flexible plastic material of a type that will not contaminate or be adversely affected by the components of the adhesive. The cup 20 has an elongated cavity 22 therein, generally cylindrical in shape with an outwardly flared upper end 23 that communicates with a circular opening 24 in the top of the cup 20 that is surrounded by an annular upper rim 25. Spaced downwardly from the rim 25 at the top of the flared passage or end 23 is an annular recess 27. The cup 20 has two integrally formed and interconnected sections, including a reservoir section 30 at the bottom of the cup 20 that substantially contains the cavity 22 and a neck section 31 that surrounds the upper flared passage 23. Both of the sections have integrally formed on opposite sides of the outside thereof a pair of wings, 32 and 33, respectively, that each provide twist grip structure that facilitates the gripping of the container 14 between two fingers in each of the hands of the dentist to twist one of the sections 30,31 relative to the other. The two sections 30,31 of the cup 20 are joined by a narrow annular web 35 that forms a weak link between the two sections 30,31. When one of the sections 30,31 is twisted relative to the other, the web 35 fractures, separating the two sections 30,31, as explained in connection with FIG. 4.

The cap 21 includes an elongated rod-like handle 40 at the top thereof with a stepped stem 41 at the bottom thereof that is in alignment with the handle 40. Between the handle 40 and the stem 41 is a disc shaped flange 42 that serves as a lid to seat against the rim 25 to close the cavity when the stem 41 is inserted through the opening 24 into the passage 23 and into the upper end of the cavity 22. The stem 41 includes an upper length 44 that is of the same diameter as that of the cavity 22 to seal against the wall thereof to prevent the flow of liquid adhesive 15 therefrom. The upper length 44 of the stem 41 overlaps only a nominal amount of about one millimeter on the wall of the cavity 22 so that only nominal compression of the contents of the cavity 22 occurs when the stem 41 of the cap 21 is inserted into the cup 20. The stem 41 also includes a lower length 45 that serves as a guide. The length 45 is of a diameter that is less than that of the cavity 22 so that it displaces only a nominal amount of the volume of the cavity 22. A outwardly projecting annular snap ring 46 encircles the upper end of the stem 44 at a distance spaced below the flange 42 an amount equal to the spacing of the recess 27 below the rim 25. The ring 46 snaps into the recess 27 to lock the cap 21 to the cup 20 when inserted therein. The insertion of the cap 21 into the cup 20 is performed after the dose 15 of adhesive is injected into the cavity 22 by moving the cap 21 relative to the cup 20 as illustrated by the arrow 48 in FIG. 2. The connection that forms between the cap 21 and the cup 20 is essentially an irreversible connection. The filled and closed container 14 is illustrated in FIG. 3.

When the container 14 is filled and closed, the interface between the cap 21 and the cup 20 forms a liquid-tight seal. However, with the snap fit connection alone, vapors of the volatile carrier can nonetheless escape with time from between the stem 44, ring 46 and flange 42 of the cap 21 and the wall of the passage 23, recess 27 and rim 25 of the cup 20. This connection is thus supplemented by the secondary seal, which may be provided in the form of the foil pouch 13 described above, or alternatively in the form of other sealing structure. For example, the flange 42 can be fusion welded or ultrasonically welded to the rim 25, or an additional sealing polymer bead 49, of a substance that does not contaminate the adhesive, can be applied between or around the junction of the rim 25 and the flange 42.

The separation of the sections 30 and 31 of the cup 20 is illustrated in FIG. 4, which shows that, by the twisting of the sections 30,31 relative to each other by applying twisting force to by way of the wings 32,33, as illustrated by the arrows 50, the sections 30,31 separate at the web 35 as the web 35 breaks. When this occurs, the guide 45 of the stem 41 keeps the stem 41 within the cavity 22 until the cap 21, along with the upper section 31 of the cup 20, is removed from the lower reservoir section 30 of the cup 20, by translating the cap 21 upwardly relative to the reservoir portion 30 of the cup 20 as illustrated by arrow 54, whereupon the cap 21 and upper cup section 31 can be discarded. The dentist, upon opening the capsule 11 in this manner, then uses the swab 12 by dipping its porous tip applicator end 55 into the cavity 22, in the direction of the arrow 57 of FIG. 5, to pick up the adhesive dose 15 from the cavity 22.

The preferred adhesive embodying principles of the present invention is a one part, one step, dental adhesive which provides strong, dependable adhesive bonds to various types of dental restorative materials and natural tooth structure. The adhesive is preferably a visible light curable, methacrylate resin-based mixture of monomers capable of forming both chemical and mechanical adhesive bonds to both natural tooth structures (enamel and dentin) and to commonly used restorative materials (composite resins, porcelain and metals). The adhesive composition includes a fast evaporating organic solvent or other carrier component, preferably ethyl alcohol based, which allows the application of the adhesive to flow into micro-fissures of the substrate smoothly. When the adhesive composition is applied, the carrier evaporates leaving a thin resin layer on the dental surface to form a tight bonding interface between tooth and restorative material.

More particularly, the one part, one step dental adhesive is comprised of the materials set forth in Table 1.

TABLE 1

| Component | Weight % |
|---|---|
| 1) ethanol | 20–25 |
| 2) bisphenol-A-bis-(2-hydroxy-3-methacryloxypropyl) ether | 17–20 |
| 3) 2-hydroxyethyl methacrylate | 17–20 |
| 4) glycerophosphate dimethacrylate | 12–14 |
| 5) barium aluminoborosilicate | 15–18 |
| 6) fumed silicon dioxide | 7–10 |
| 7) sodium hexafluorosilicate | 0.5–1.0 |
| 8) 2-(ethylhexyl)-4-(dimethylamino) benzoate | 0.5–1.0 |
| 9) camphorquinone | 0.25–0.5 |
| 10) 2,6-di (tert.-butyl)-4-hydroxytoluene | 0.01–0.02 |

The adhesive composition has a pH of 2.5–3.0, and a refractive index of 1.45–1.46. The Brookfield viscosity of the adhesive is 162–175 cps. The composition includes particle or bead fill of 22–28% by weight. The barium aluminoborosilicate is preferably a treated fill (TF) made from SP-345 glass ground to a particle size that averages approximately 0.6 microns. The TF and the fumed silicon dioxide are preferably treated with a silane coupling agent such as A-174. The fumed silicon dioxide is preferably OX-50 of about 0.04 micron particle size and the very fine TS-530.

Unlike the multi part Optibond adhesives discussed above, phthalic acid monomethacrylate (PAMA) is omitted from the composition.

Components such as glycerol dimethacrylate (GDM), which is present in multi part adhesives, is preferably omitted also. Further, BA-20 radiopaque barium glass fill of the multi part Optibond adhesive is not included in the fill and the particle size of the included fill is substantially reduced from that of the multi part adhesive composition.

Tests have demonstrated that the adhesive within the ranges set forth in Table 1 above satisfactorily seals a tooth so that there is no gap between the tooth surface and the restorative material. Further tests have demonstrated that, whether applied to etched dentin or unetched dentin, leakage was 0% in the shoulder area of the dentin, in the axial area of the dentin, and in the enamel, even when stress was applied. Thus, the bonding agent appears to be quite strong and undergoes no leakage even when exposed to stress.

The adhesive composition also incorporates a fluoride release system such that six parts per million of fluoride ions are released in a one-month period. This is advantageous as compared to the other adhesives which contain no fluoride release system. Further, the adhesive composition according to this invention includes fillers which are not included in the other one part adhesive compositions.

The adhesive of the preferred embodiment of the invention uses ethanol as a carrier and solvent and the GPDM as an adhesion promoter. The specific preferred composition of the adhesive is set forth in Table 2.

TABLE 2

| | Component | % Weight |
|---|---|---|
| ETOH | ethanol | 22.91 |
| BISGMA | bis-phenol-A-bis-(2-hydroxy-3-methacryloxypropyl) ether | 18.00 |
| HEMA | 2-hydroxyethyl methacrylate | 18.00 |
| GPDM | glycerophosphate dimethacrylate | 13.09 |
| TF | barium aluminoborosilicate (treated filler) | 17.05 |
| TS530 | fumed silicon dioxide | 1.82 |
| OX50 | treated fumed silicon dioxide | 7.12 |
| $Na_2SiF_6$ | sodium hexafluorosilicate | 0.96 |
| ODMAB | 2-(ethylhexyl)-4-(dimethylamino) benzoate | 0.751 |
| CQ | 1,7,7-Trimethylbicyclo-[2.2.1]-hepa-2,3-dione | 0.327 |
| BHT | 2,6-di(tert.-butyl)-4-methylphenol | 0.01309 |

Those skilled in the art will appreciate that the application of the present invention herein are varied, and that the invention is described in preferred embodiments Accordingly, additions and modifications can be made without departing from the principles of the invention. Accordingly, the following is claimed:

What is claimed is:

1. A dental adhesive delivery system comprising:

an elongated adhesive applicator having a handle for manually holding the applicator and an applicator tip for transferring adhesive from a reservoir onto dental anatomy of a patient;

a single dose container having a a body having a wall with a sealed openable end, the wall defining a reservoir section having a cavity therein accessible from the openable end;

the cavity containing a one-part dental adhesive for use with a single patient in a single-dose amount that is in the order of from 0.05 to 1.0 milliliters in volume; and said openable end, when opened, forming an opening dimensioned to permit insertion of the applicator tip through the opening and into the cavity for the transfer of the adhesive from the cavity onto the applicator tip for withdrawal of the applicator tip from the cavity with the transferred adhesive thereon for further transfer of the adhesive to, and the application of the adhesive onto, the dental anatomy of the patient.

2. The dental adhesive delivery system of claim 1 further comprising:

a vapor impervious package enclosing the container.

3. The dental adhesive delivery system of claim 1 wherein:
   the adhesive within the container is alcohol based.
4. The dental adhesive delivery system of claim 1 wherein:
   the adhesive within the container has a filler content of between 22 and 28% by weight.
5. The dental adhesive delivery system of claim 1 wherein:
   the adhesive within the container has a filler content of approximately 26% by weight.
6. The dental adhesive delivery system of claim 1 wherein the adhesive has a composition of approximately 20–25% by weight ethanol, 17–20% by weight bisphenol-A-bis-(2-hydroxy-3-methacryloxypropyl) ether, 17–20% by weight 2-hydroxyethyl methacrylate, 12–14% by weight glycerophosphate dimethacrylate, 15–18% by weight barium aluminoborosilicate, 7–10% by weight fumed silicon dioxide, 0.5–1.0% by weight sodium hexafluorosilicate, 0.5–1.0% by weight 2-(ethylhexyl)-4-(dimethylamino) benzoate, 0.25–0.5% by weight camphorquinone and 0.01–0.02% by weight 2,6-di (tert.butyl)-4-hydroxytoluene.
7. The delivery system of claim 1 wherein the amount of the single dose adhesive filling the cavity is a single tooth dose of approximately 0.1 ml.
8. The delivery system of claim 1 wherein the volume of the cavity is not more than approximately one milliliter.
9. The delivery system of claim 1 wherein the amount of the single dose adhesive filling the cavity is a single dose of not more than approximately one milliliter.
10. The delivery system of claim 1 wherein the volume of the cavity is approximately 0.1 ml.
11. The dental adhesive delivery system of claim 1 wherein:
    the adhesive includes a volatile adhesive carrier; and
    the system further comprises a vapor seal containing adhesive carrier vapors in or about the container.
12. A method of providing a dental adhesive for bonding a dental restoration to dental anatomy of a patent, the method comprising the steps of:
    providing a single dose container having:
       an elongated body defined by a tubular wall surrounding a longitudinal bore accessible from an opening in one end of the body surrounded by a rim, the body having finger twist grip structure on the outside thereof, and
       a closure having an elongated handle at a proximate end thereof, a tip at a remote end thereof, a tubular plug section between the handle and the tip that is dimensioned to close the opening when the closure is inserted tip first into the bore and a flange larger than the opening between the handle and the plug section form a liquid tight seal with the rim;
    loading the bore with a single dose of a one part dental adhesive; and
    inserting the plug section of the closure through the opening and into the bore until the flange forms the seal against the rim.
13. A method of providing a single dose dental adhesive application kit comprising the step of providing at least one container sealed and loaded according to the method of claim 12 and further comprising the step of:
    providing an elongated applicator having an applicator end adapted to fit into the bore and coat with adhesive from the cavity.
14. A method of applying a dental adhesive to the dental anatomy of a patient comprising the steps of providing a single dose dental adhesive kit according to the method of claim 13 and further comprising the steps of:
    gripping the twist structure and handle respectively with the fingers of opposite hands and twisting the closure relative to the body to open the container and then translating the closure out of the bore;
    dipping the applicator end of the applicator into the bore to coat with adhesive; and
    transferring adhesive with the applicator onto an area of the surface of the dental anatomy of a patient to coat the area of the surface with the adhesive.
15. A method of fitting a patient with a dental restoration comprising the steps of applying a dental adhesive to the dental anatomy according to the method of claim 14 the method further comprising the steps of:
    affixing a dental restoration to the dental anatomy by contacting the adhesive coated surface with the restoration and setting the adhesive.
16. The method of claim 12 wherein the loading step further comprises the step of:
    loading the bore with an alcohol based adhesive.
17. The method of claim 12 wherein the loading step further comprises the step of:
    loading the bore with a volatile organic carrier based adhesive; and
    forming a vapor tight seal to contain vapors of the carrier in or about the container.
18. The method of claim 12 wherein the loading step further comprises the step of:
    loading the bore with an adhesive having a fiber fill of between 22% and 28%.
19. The method of claim 12 wherein the loading step further comprises the step of:
    loading the bore with an alcohol based adhesive having a fiber fill of between 20% and 30%.
20. The method of claim 12 wherein:
    the providing step includes the step of providing a non-resealable container having the elongated body wherein the finger twist grip structure includes two longitudinally spaced structure sections and the tubular wall includes a fracturable annular web separating the structure sections; and
    the method further comprises the step of gripping the two sections of twist structure with the fingers of opposite hands and twisting the closure relative to the body to fracture the tubular wall at the annular web to open the container.
21. A single dose dental adhesive delivery system comprising:
    a single dose container having:
       an elongated body defined by a tubular wall surrounding a longitudinal bore accessible from an opening in one end of the body surrounded by a rim, the body having finger twist grip structure on the outside thereof, and
       a closure having an elongated handle at a proximate end thereof, a tip at a remote end thereof, a tubular plug section between the handle and the tip that is dimensioned to close the opening when the closure is inserted tip first into the bore and a flange larger than the opening between the handle and the plug section form a liquid tight seal with the rim;
    a single dose of a one part dental adhesive in the bore; and
    the plug section of the closure being inserted through the opening and into the bore until the flange forms the seal against the rim.

22. The single dose dental adhesive delivery system of claim 21 wherein:

the adhesive is a volatile organic carrier based adhesive; and the system further comprises a vapor seal containing adhesive carrier vapors in or about the container.

23. The single dose dental adhesive delivery system of claim 21 wherein:

the adhesive includes a fiber fill of between 22% and 28%.

24. The single dose dental adhesive delivery system of claim 21 wherein:

the adhesive is an alcohol based adhesive having a fiber fill of between 20% and 30%.

25. A kit comprising the single dose dental adhesive delivery system of claim 21 and further comprising:

an elongated applicator having an applicator end adapted to fit into the bore and coat with adhesive from the cavity.

26. The delivery system of claim 21 wherein the container that is provided is non-resealable.

27. A single patient dental adhesive delivery system comprising:

a non-reusable sealed container including:

an elongated body defined by a tubular wall surrounding a longitudinal bore having an opening in one end of the body surrounded by a rim, the tubular wall including two longitudinally spaced sections and a fracturable annular web separating the sections; and a closure having an elongated handle at a proximate end thereof, a tip at a remote end thereof, a tubular plug section between the handle and the tip that is dimensioned to close the opening when the closure is inserted tip first into the bore and a flange larger than the opening between the handle and the plug section form a liquid tight seal with the rim;

the plug section of the closure situated in the opening and extending into the bore with the flange forming a seal against the rim with the tip and tubular wall enclosing a cavity within the container;

a single patient adhesive dose including a volatile adhesive carrier contained within the sealed container; and a vapor seal surrounding and enclosing the container and containing adhesive carrier vapors in or about the container.

28. The delivery system of claim 27 wherein:

the adhesive dose contained in the sealed container is a dose in the approximate range of 0.05 to 1.0 ml.

29. The delivery system of claim 27 wherein:

the adhesive dose contained in the sealed container is a dose of approximately 0.1 ml.

30. A method of providing a one-part dental adhesive for bonding a dental restoration to dental anatomy of a single patent and bonding the restoration to the dental anatomy therewith, the method comprising the steps of:

providing a single-dose container having a wall surrounding a cavity having an opening;

loading the cavity through the opening with a one part dental adhesive in a single dose having a volume of from approximately 0.05 to approximately 1.0 milliliter;

sealing the opening with a closure to form a closed surface surrounding the cavity;

opening the container such that at least a lower portion of the wall forms a section containing the single dose of dental adhesive and having an open end dimensioned to receive an applicator therethrough;

inserting an applicator through the open end into the cavity, contacting the adhesive with the applicator and transferring adhesive from the cavity to the applicator for removal of the adhesive from the cavity for transfer to and application of adhesive onto the dental anatomy of the patient;

removing a single dose of the adhesive from the cavity with the applicator;

applying the single dose of adhesive with the applicator to the dental anatomy of a single patient.

31. The method of claim 30 wherein:

the opening step includes the step of breaking open the container by permanently and non-resealably breaking the closed surface; and the method further comprises the step of disposing of the container and the applicator after applying the adhesive to the dental anatomy of the single patient without applying adhesive from the container to the dental anatomy of any other patient.

32. The method of claim 30 wherein:

the sealing step includes the steps of providing a closure having an plug section and a handle, and inserting the plug section into the opening; and the separating step includes the step of separating the closure from a lower portion of the container by dividing the wall of the cavity into two portions, including an upper portion which remains connected to the closure and a lower portion which forms the section containing the single dose of adhesive.

33. The method of claim 30 wherein:

the sealing step includes the steps of providing a closure having a plug section and a handle, and inserting the plug section into the opening; and the separating step includes the step of separating the closure from at least a portion of the body to form the section containing the single dose of adhesive having a volume greater than the volume of the single dose of the adhesive such that the open end of the cavity extends away from the volume of the adhesive in the section to provide a space for receiving the applicator into the cavity without causing overflow of adhesive from the cavity.

* * * * *